(12) United States Patent
Singh

(10) Patent No.: US 7,235,269 B2
(45) Date of Patent: *Jun. 26, 2007

(54) BOWMAN-BIRK INHIBITOR CONCENTRATE PRODUCT AND PROCESS

(75) Inventor: Navpreet Singh, St. Louis, MO (US)

(73) Assignee: Solae, LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/693,433

(22) Filed: Oct. 24, 2003

(65) Prior Publication Data

US 2004/0131711 A1    Jul. 8, 2004

Related U.S. Application Data

(60) Provisional application No. 60/421,354, filed on Oct. 25, 2002.

(51) Int. Cl.
*A61K 36/00* (2006.01)
(52) U.S. Cl. .................. 424/757; 424/776; 435/213
(58) Field of Classification Search ............. 424/757, 424/776; 435/213
See application file for complete search history.

(56) References Cited

U.S. PATENT DOCUMENTS

| 4,793,996 A | 12/1988 | Kennedy et al. |
| 5,217,717 A | 6/1993 | Kennedy et al. |
| 5,505,946 A * | 4/1996 | Kennedy et al. |
| 6,887,498 B2 * | 5/2005 | Konwinski et al. ......... 424/757 |
| 2003/0064121 A1 | 4/2003 | Konsinski et al. |

* cited by examiner

*Primary Examiner*—Susan Hoffman
(74) *Attorney, Agent, or Firm*—James L. Cordek; Holly M. Amjad; Cary A. Levitt

(57) ABSTRACT

A Bowman Birk Inhibitor (BBI) concentrate including at least 50% soy protein by weight of dry matter; and a chymotrypsin inhibitor activity level of at least 200 milligrams of chymotrypsin inhibited per gram of dry matter of product. A method of making a BBI concentrate including the steps of providing acid extracted solubles from a defatted soybean material; mixing acetone with the acid extracted solubles to form a precipitate mixture; separating the precipitate from the mixture of acetone and acid extracted solubles; diluting the separated precipitate with water to form an aqueous solution; ultrafiltering the aqueous solution to obtain a retentate. The defatted soybean material may be defatted soybean flakes or flour. The step of providing acid extracted solubles includes slurrying the defatted soybean flakes with water to form slurry, adjusting the pH of the slurry to 4.0 to 6.5 using hydrochloric acid and separating the solubles from the slurry.

9 Claims, No Drawings

BOWMAN-BIRK INHIBITOR CONCENTRATE PRODUCT AND PROCESS

PRIORITY REFERENCE

This application claims the benefit of priority under 35 U.S.C. §119(e) to provisional application Ser. No. 60/421,354, filed Oct. 25, 2002.

BACKGROUND OF THE INVENTION

1. Field of the Invention

This invention generally relates to Bowman-Birk Inhibitor (BBI) and more particularly to a Bowman-Birk Inhibitor Concentrate (BBIC) extracted from soybeans, a method of producing a Bowman-Birk Inhibitor Concentrate (BBIC) and products containing the Bowman-Birk Inhibitor Concentrate (BBIC).

2. Description of the Related Art

Bowman-Birk Inhibitor (BBI) is an enzyme-inhibitor described by Bowman (*Proc. Soc. Exptl. Med.*, 63:547 (1946)) and Birk et al. (*Bull. Res. Council Israel*, Sec. A 11:59 (1962) and *Biochem. Biophys. Acta*, 67:326 (1963)), and is found in crude soybean extract. Bowman-Birk Inhibitor (BBI) has been shown to exhibit inhibitory activity against the malignant transformation of cells under certain conditions and its administration has been shown to affect various forms of cancer. It has been demonstrated that the Bowman-Birk Inhibitor (BBI) exhibits certain physiological activity that prevents, or at least greatly reduces, radiologically or chemically induced malignant transformation of cells in culture and in laboratory animals. Yavelow et al. (*Proc. Natl. Acad. Sci.*, USA 82:5395–5399 (1985)) reported that a crude soybean extract, if defatted with acetone, effectively blocked cell transformation in vitro. An active component of this crude extract is the BBI. These observations, along with epidemiological data, suggest the use of BBI as a putative dietary anticarcinogen, particularly with respect to colon cancer.

Weed et al. (*Carcinogenesis*, 6:1239–1241 (1985)) disclose that an extract of soybeans containing the Bowman-Birk protease inhibitor, when added to the diet of dimethylhydrazine (DMH)—treated mice, resulted in significant suppression of odenomatous tumors of the colonic mucosa. DMH—induced colon cancer in mice is generally regarded as an excellent animal model for the human disease, because the DMH carcinogen treatment induces adenocarcinomas of the mouse colon and rectum, which are similar to the tumors arising in the human colon. These results suggest that a dietary additive of the sort studied might confer some protection against the development of human colon cancer without undesirable side effects. The BBI extract and methods for its preparation were as described by Yavelow et al. *Cancer Res.*, 43:2454–2459 (1983); *Proc. Natl. Acad. Sci.*, USA 82:5395–5399 (1985) and Hwang et al. *Biochem. Biophys. Acta*, 495:369–382 (1977).

Massadi et al. (*JNCI*, 76:447–452 (1986)) demonstrated that a soybean extract containing the protease inhibitor BBI suppresses 7,12-dimethyl-benz[a]anthracene (DMBA)—induced carcinogenesis in the hamster cheek pouch. This oral cancer model, with the use of the hamster cheek pouch carcinogenesis system, has the same histopathology, growth pattern, and precancerous lesions as the most common form of human oral cancer, squamous cell carcinoma. This study demonstrates that hamster cheek pouch carcinogenesis can be inhibited by BBI and suggests that human oral carcinogenesis might respond to BBI in a comparable manner. The BBI preparation used in this study was a crude extract of the inhibitor prepared as described by Yavelow et al. (*Proc. Natl. Acad. Sci.*, USA 82:5395–5399 (1985)).

Baturay et al. (*Cell Biology and Toxicology*, 2:21–32 (1986)) disclose that a BBI preparation, derived from a crude soybean extract defatted with acetone, suppresses radiation and chemically induced transformation in vitro, with or without enhancement by the co-carcinogen, pyrene. Yavelow et al., 1985, supra show that either pure BBI or the BBI extract prepared in accordance with their methods suppresses radiation-induced transformation in $C_3H_{10}T½$ cells. Kennedy et al, Proc. Nat'l. Acad. Sci. USA 1984, 81, 1827–39, report that either pure BBI or the BBI extract prepared in accordance with their method reduce the levels of chromosome abnormalities in cells of patients with Bloom's syndrome (a genetic disease in which the high levels of chromosome abnormalities are thought to predispose the patients to a higher than normal cancer incidence). Still, other studies suggest that soybean-derived protease inhibitors can have suppressive effects on skin, breast, and liver carcinogenesis in vivo.

Kennedy et al. in *Anticarcinogenesis and Radiation Protection*, edited by Cerutti et al., Plenum Pub. Co., pp. 285–295 (1987), disclose that carcinogenesis in various systems is suppressed using a crude BBI extract prepared by defatting soybeans with acetone. Their results suggested that very low concentrations of BBI-type protease inhibitor preparation would be effective as chemopreventative agents for colon cancer. There was no evidence to suggest that the use of protease inhibitors as chemopreventative agents would be complicated by possible toxicity problems.

St. Clair et al. (*Cancer Res.*, 50:580–586 (1990)) report that the addition of 0.5% or 0.1% semi-purified BBI or 0.1% or 0.01% purified BBI to the diet of DMH-treated mice resulted in a statistically significant suppression of angiosarcomas and nodular hyperplasia of the liver and colon carcinogenesis. The results of this study also indicate that BBI, included as 0.5% of the diet or less, had no adverse effect upon the health of the mice, but had capacity to suppress liver and colon carcinogenesis.

Perlmann et al. (*Methods in Enzymology*, 19:860–861 (1970)) have described an elaborate method for obtaining the BBI from a defatted soybean extract.

U.S. Pat. No. 4,793,996 to Kennedy et al. discloses a process comprising treating soybeans with acetone, followed by ethanol extraction and acetone precipitation for obtaining BBI. The soybeans may be defatted prior to acetone treatment. In addition, BBI may be further purified by conventional techniques. Kennedy et al. discovered that in the conventional process for preparing BBI from soybeans, a factor remained which adversely affected the ability of BBI to inhibit the malignant transformation of cells. If the factor was removed, the resulting BBI product was capable of inhibiting the malignant transformation of cells. It was found to be possible to remove this factor by treating the soybeans with acetone prior to the ethanol extraction step taught by Perlmann et al. (supra)

Kennedy et al. teach that it is unnecessary to carry out a procedure requiring complete purification of the extract to the point where the product contains only a single protein, but instead determined that it was sufficient to stop the purification procedure at a point where a crude inhibitor extract is obtained. This crude extract (i.e., concentrate) is itself edible and can be used as an inhibitor of malignant transformation of cells by oral ingestion. Kennedy et al. disclose a process for preparing a crude soybean extract containing an inhibitor of malignant cell transformation which comprises defatting soybeans by bringing them into contact with at least an equal weight of acetone, and extracting the inhibitor from the defatted soybeans with alcohol, thus producing a crude inhibitor extract having greatly increased effectiveness.

U.S. Pat. No. 5,217,717 to Kennedy et al. discloses a method for producing BBI concentrate from soybean solubles without aqueous alcohol extraction by centrifugation and ultrafiltration, and further purification by acetone precipitation. This patent also teaches that the less solvent used, the more economical and safer the process. Waste-solvent streams containing a mixture of alcohol-water-acetone require very complex and expensive distillation equipment for separation of the solvents.

The presence of BBI is commonly measured by the level of chymotrypsin inhibition (CI). The present invention provides a new method for making an acetone-extracted Bowman-Birk Inhibitor concentrate having at least 50% soy protein by weight of dry matter and a chymotrypsin inhibitor (CI) level of at least 200 milligrams/gram.

SUMMARY OF THE INVENTION

The present invention provides a method of making a Bowman-Birk Inhibitor concentrate. The method, in one form thereof, comprises the steps of providing acid extracted solubles from a defatted soybean material; mixing acetone with the acid extracted solubles to form a precipitate; separating the precipitate from the mixture of acetone and acid extracted solubles; diluting the separated precipitate with water to form an aqueous solution; and ultrafiltering the aqueous solution to obtain a retentate.

In one embodiment, the defatted soybean material comprises defatted soybean flakes, and the step of providing acid extracted solubles includes slurrying the defatted soybean flakes with water to form a slurry and adjusting the pH of the slurry to 4.0 to 6.5 using hydrochloric acid. In a related embodiment, the acid extraction is performed at a pH of 4.5. Alternatively, the acid extraction is performed at a pH of 5.4.

The present invention provides an acetone extracted Bowman-Birk Inhibitor concentrate comprising at least 50% soy protein by weight of dry matter; and a chymotrypsin inhibitor level of at least 200 milligrams/gram.

The present invention also provides a pharmaceutical composition and a dietary supplement comprising a BBI concentrate made according to a method of the present invention.

DETAILED DESCRIPTION OF THE INVENTION

The present invention is directed to a method for making a Bowman-Birk Inhibitor (BBI) product demonstrating a high level of chymotrypsin inhibition (CI) activity. The method of the present invention provides a method of making the BBI product concentrate without the conventional alcohol extraction. The method generally includes the steps of providing acid extracted solubles from a defatted soybean material; mixing acetone with the acid extracted solubles to form a precipitate; separating the precipitate from the mixture of acetone and acid extracted solubles; diluting the separated precipitate with water to form an aqueous solution; and ultrafiltering the aqueous solution to obtain a retentate.

The acid extracted solubles may be recovered directly from defatted soy flakes or flour using any commercial acid-leached soy protein concentrate process. The defatted soy flakes or flour may be obtained either commercially, or by flaking dehulled soybeans and defatting the flakes with hexane in a conventional manner to remove soybean oil. The defatted soy flakes are slurried with water to form a slurry having a solid content of between about 5–15 wt. %. However, a slurry having even lower solids content could be employed. Although not necessary, it may be beneficial to pre-heat the water to about 94° C. prior to adding to the flakes. It may also be beneficial to agitate the slurry.

The acid extraction may be performed by adjusting the pH of the slurry to between 4.0 to 6.5 by adding an acid. The slurry may then be agitated for about one hour, after which the solubles are separated from the slurry. In a preferred embodiment, the solubles are separated using a decanting centrifuge. In a preferred embodiment, acid extraction is performed at a pH of 4.5. In another embodiment, acid extraction is performed at a pH of between 5.0–5.4. In a preferred embodiment, the acid used is hydrochloric acid.

Acetone is then mixed with the acid extracted soybean solubles to form a precipitate. The acetone is added in an amount sufficient to form the precipitate. Acetone in amounts between 0.5 to 3 times by weight of the solubles and, more preferably, 2 times the amount by weight of the solubles is useful in forming the precipitate. The resulting precipitate is separated from the mixture of acetone and acid extracted solubles by decanting or separating the liquid from the mixture. The step of mixing acetone with the acid extracted solubles may include agitating the mixture of acetone and acid extracted solubles for between about 5–15 minutes, preferably, about 10 minutes. The acetone acid extracted solubles mixture is then allowed to settle, for preferably at least one hour, and the precipitate is separated as described above.

According to an alternative method, the separated precipitate may be washed with acetone prior to diluting the precipitate with water. In this step, the separated precipitate is slurried with acetone and the precipitate is subsequently collected from the acetone by decanting or separating the acetone from the slurry of acetone and precipitate. In this alternative embodiment, the amount of acetone slurried with the collected precipitate may be the same as the amount of acetone mixed with the acid extracted solubles, but is preferably half the amount that was mixed with the acid extracted solubles.

The precipitate is then diluted with water to form an aqueous solution and the aqueous solution is passed through an ultrafiltration membrane system to yield a retentate having a high concentration of Bowman Birk Inhibitor. A spiral wound membrane with a molecular weight cutoff (MWCO) from about 1,000 to about 20,000 is suitable for use in this ultrafiltration step. A membrane having a MWCO of about 1,000 to about 5,000 is particularly useful in this ultrafiltration step. The resulting retentate may then be spray dried to form a BBI concentrate having high level of CI.

Suitable membranes of different molecular weight cutoffs are readily and commercially available from several vendors, such as Koch Membrane Systems of Wilmington, Mass.; Osmonics of Minnetonka, Minn.; PTI Advanced Filtration of Oxnard, Calif.; and Synder Filtration of Vacaville, Calif.

In another embodiment, the precipitate may be vacuum filtered prior to the ultrafiltration step using any conventional vacuum filtration system. In one embodiment, the precipitate is vacuum filtered using Buchner funnel and filter paper. In another embodiment, a rotary vacuum filter could be used for filtering the precipitate.

The resulting product includes at least 50% soy protein by weight of dry matter and has a chymotrypsin inhibitor (CI) level of at least 200 milligrams/gram. The resulting BBI product is useful as a pharmaceutical composition or dietary supplement.

The Bowman-Birk Inhibitor product produced by the present invention has use as pharmaceutical compositions and dietary supplements. Compositions made in accordance with the various embodiments of the invention are useful for inhibiting the malignant transformation of cells by administering a BBI concentrate. The compositions are useful for preventing cancer or inhibiting cancer progression in mammals, including humans, by administering the compositions, either alone or in combination with a pharmaceutically acceptable carrier. The compositions can be orally administered, either as prophylactic dietary supplements or pharmaceuticals.

The amount of Bowman-Birk Inhibitor ("BBI") in the product was characterized by the measurement of Chymotrypsin Inhibitor ("CI") activity, which is an indirect assay for BBI. The method used for CI analysis is based on the American Oil Chemists' Society (AOCS) official method Ba 12–75 for trypsin inhibitor activity for soy products, differing in the enzyme and substrate used. The substrate used for CI analysis is N-Glutaryl-L-phenylalanine p-nitroanilide (GPNA), available from Sigma-Aldrich as product number 49738. The enzyme used is α-Chymotrypsin from bovine pancreas (Enzyme Commission (EC) Number: 3.4.21.1), available from Sigma-Aldrich as product number C4129. The AOCS method is based upon Kakade et al. (*Cereal Chemistry*, 51.376 (1974)). Chymotrypsin hydrolyzes the substrate N-Glutaryl-L-phenylalanine-p-nitroanilide present in excess. The release of p-nitroanilide, a yellow dye, is measured spectrophotometrically. In the presence of soy protein product, the release of p-nitroanilide changes inversely with the level of active chymotrypsin inhibitor activity. CI activity is reported as milligram (mg) of Chymotrypsin inhibited per gram of the product.

These and other aspects of the present invention may be more readily understood by reference to the following example which illustrates the practice of the invention, and the characterization and utility of products resulting therefrom. In the examples and throughout percentages are given by weight on moisture-free basis (mfb) unless otherwise indicated.

EXAMPLE 1

About 100 kg (220 lb) of defatted soybean flakes (white flakes) were mixed with 587.3 kg (156 gallons) of water. The pH of the mixture was adjusted to 5.4 using food grade hydrochloric acid. After mixing for one hour, the slurry was centrifuged using a Sharples P660 continuous decanter centrifuge. The centrifuge feed rate was 7.57 L/min (2 gpm), and the differential backdrive speed was 20 rpm. A total of 421.4 kg (929 lb) of centrate was collected in a tank, to which 842.32 kg (1857 lb) of acetone was added with mixing. After 10 minutes mixing time, the mixing was stopped and the insoluble material was allowed to settle. After 1 hour, the liquid layer was decanted, and 421.4 kg (929 lb) of acetone was added to the insoluble material with mixing. Again, after 10 minutes mixing time, the mixing was stopped and the insoluble material was allowed to settle. After 1 hour, the liquid layer was decanted, and approximately 299.3 kg (660 lb) of the precipitated material remained in the tank. The precipitated material was vacuum filtered to remove acetone and acetone-soluble material and then air dried. After air drying, the precipitated material was dispersed in water and the resulting aqueous solution was ultrafiltered using a 2,000 molecular weight cut-off (MWCO) spiral wound membrane. The retentate from the ultrafiltration process was spray dried. The dried product was analyzed to determine the composition, and the chymotrypsin inhibitor (CI) activity was determined according to the procedure described herein. The results of the analysis are shown in TABLE 1.

TABLE 1

| Composition of product derived from the method of EXAMPLE 1 | |
|---|---|
| CI (mg Chymotrypsin Inhibited/g of product, mfb) | 252.74 |
| Protein (wt. %, mfb) | 64.63 |
| Ash (wt. %, mfb) | 16.80 |

EXAMPLE 2

About 50 kg (110 lb) of defatted soybean flakes (white flakes) were mixed with 295 liters (78 gallons) of water, pre-heated to 32° C. (90° F.). The pH of the mixture was adjusted to 4.5 using food grade hydrochloric acid. During mixing, 20 liters of 3% hydrogen peroxide was slowly added. After mixing for one hour, the slurry was centrifuged using a Sharples P660 continuous decanter centrifuge at a feed rate of 7.57 L/min (2 gpm). The centrifuge had ring dam setting of 4 and was run at 2500 rpm. A total of 171.9 kg (379 lb) of centrate was collected in a tank, to which 343.8 kg (758 lb) of acetone was added with mixing. After 10 minutes mixing time, the mixing was stopped and the precipitated material was allowed to settle. After 1 hour, the liquid layer was decanted, and 171.9 kg (379 lb) of acetone was added to the precipitated with mixing. Again, after 10 minutes mixing time, the mixing was stopped and the precipitated material was allowed to settle. After 1 hour, the liquid layer was decanted, and the precipitated material remaining the tank was collected. This material was vacuum filtered to remove acetone and acetone-soluble material using Whatman # 1 filter and buchner funnel and then air dried. After air drying, the material was dispersed in 567.8 (150 gallons) of water and the resulting aqueous solution was transferred to a membrane feed tank through a 100-mesh (149 μm) strainer. The suspension was fed to an ultrafiltration membrane system containing two spiral-wound membranes, one of 2,000 MWCO and the other of 5,000 MWCO. The temperature of the suspension was maintained at about 26.7° C. (80° F.) during membrane processing. About 90% of the original feed volume added to the membrane feed tank was removed as permeate. The retentate from the ultrafiltration process was spray dried. The dried product was analyzed to determine the composition, and the chymotrypsin inhibitor (CI) activity was determined according to the procedure described herein. The results of the analysis are shown in TABLE 2.

TABLE 2

| Composition of product derived from the method of EXAMPLE 2 | |
|---|---|
| CI (mg Chymotrypsin Inhibited/g of product, mfb) | 390.89 |
| Protein (wt. %, mfb) | 67.94 |
| Ash (wt. %, mfb) | 16.98 |

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as set forth in the following claims.

What is claimed is:

1. A method of making a Bowman-Birk Inhibitor concentrate, comprising the steps of:
   providing acid extracted solubles from a defatted soybean material;
   mixing acetone with the acid extracted solubles to form a precipitate, agitating the acetone-precipitate for about 1 hour and allowing the acetone-precipitate mixture to settle;
   separating the precipitate from the mixture of acetone and acid extracted solubles;
   washing the separated precipitate with acetone by slurrying said separated precipitate in acetone and subsequently removing said acetone from said precipitate by vacuum filtering;
   diluting the separated precipitate with water to form an aqueous solution;
   ultrafiltering the aqueous solution to obtain a retentate; and
   drying the retentate to obtain the Bowman-Birk Inhibitor concentrate.

2. The method of claim 1 wherein the defatted soybean material comprises defatted soybean flakes or defatted soybean flour.

3. The method of claim 2 wherein said step of providing acid extracted solubles includes slurrying the defatted soybean flakes with water to form a slurry.

4. The method of claim 3 wherein said step of providing acid extracted solubles includes adjusting the pH of the slurry to 4.0 to 6.5 using hydrochloric acid.

5. The method of claim 4, wherein said step of providing acid extracted solubles includes separating the acid extracted solubles from the slurry.

6. The method of claim 1, wherein the amount of acetone mixed with the acid extracted solubles is between half and four times the amount by weight of the acid extracted solubles.

7. The method of claim 6, wherein the amount of acetone mixed with the acid extracted solubles is 2 times the amount by weight of the acid extracted solubles.

8. The method of claim 1, wherein the amount of acetone mixed with the acid extracted solubles is between half and two times the amount by weight of the acid extracted solubles.

9. The method of claim 8, wherein the amount of acetone used to wash the precipitate is half the amount mixed with the acid extracted solubles.

* * * * *